(12) United States Patent
Peter et al.

(10) Patent No.: US 8,389,218 B2
(45) Date of Patent: Mar. 5, 2013

(54) ANALYSIS OF SINGLE NUCLEOTIDE POLYMORPHISMS USING A NICKING ENDONUCLEASE

(75) Inventors: Brian Jon Peter, Los Altos, CA (US); Nicholas M. Sampas, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 484 days.

(21) Appl. No.: 12/541,032

(22) Filed: Aug. 13, 2009

(65) Prior Publication Data

US 2011/0039716 A1   Feb. 17, 2011

(51) Int. Cl.
*C12Q 1/68* (2006.01)
*C12N 15/11* (2006.01)
*C07H 21/04* (2006.01)

(52) U.S. Cl. .... 435/6.11; 435/6.1; 536/24.3; 536/24.31; 536/24.32

(58) Field of Classification Search ........................ None
See application file for complete search history.

(56) References Cited

U.S. PATENT DOCUMENTS

2007/0178470 A1* 8/2007 Bissonnette et al. .............. 435/6
2009/0035762 A1   2/2009 Sampas

OTHER PUBLICATIONS

Kiesling, T., et al. Sequence specific detection of DNA using nicking endonuclease signal amplification (NESA). Nucleic Acids Research. 2007, vol. 35, No. 18, pp. e117.
Xiao, M., et al. Rapid DNA mapping by fluorescent single molecule detection. Nucleic Acids Research. 2007, vol. 35, No. 3, pp. e16.

* cited by examiner

*Primary Examiner* — James Martinell

(57) ABSTRACT

A method of genome analysis is provided. In certain embodiments, the method comprises: a) contacting a double-stranded genomic DNA with a site-specific nicking endonuclease that recognizes a sequence comprising a single nucleotide polymorphism (SNP), in which the endonuclease nicks the genomic DNA at a nick site only if a first allele of the SNP is present; b) denaturing the genomic sample; c) contacting the denatured genomic sample with an array comprising a first probe and a second probe, in which nicking results in less binding of the denatured sample to the first probe relative to a sample that is not nicked; and d) comparing the amount of hybridization to the first probe to the amount of hybridization to said second probe, in which decreased binding of the denatured genomic samples to the first probe relative to the second probe indicates that the first allele of the SNP is present.

20 Claims, 3 Drawing Sheets

Fig. 2
A.
A/C SNP in Nb. Bsm I nicking site
B. If SNP = A:
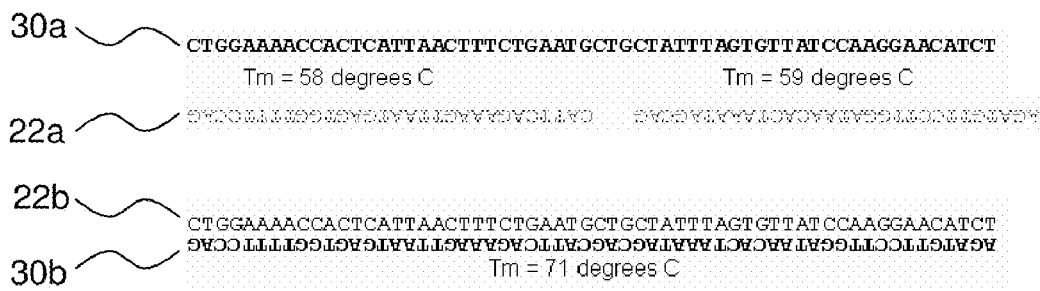
C. If SNP = C
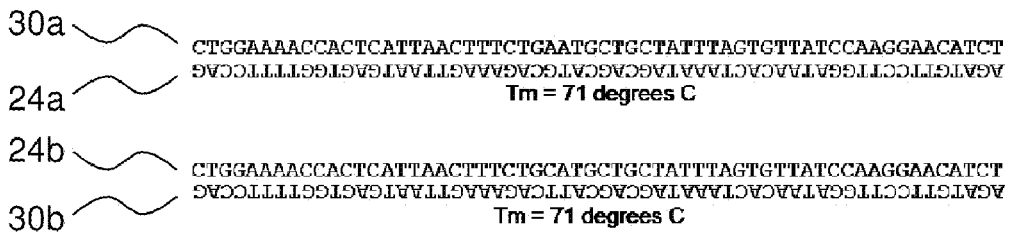

ANALYSIS OF SINGLE NUCLEOTIDE POLYMORPHISMS USING A NICKING ENDONUCLEASE

The human genome has several types of variation which confer genetic differences between individuals. Single nucleotide polymorphisms (SNPs) are sites of single base changes which vary in at least 1% of the population. Copy number variants (CNVs) are larger regions of DNA which are duplicated or deleted with respect to a reference genome. Measurements which incorporate both SNP and CNV measurements can be referred to as allele-specific copy number measurements.

Allele-specific copy number measurements are important to the research community for the diagnosis of disease, especially in cytogenetics and cancer. Methods for the accurate detection of alleles and quantitation of their respective copy numbers allow the screening of many distinct candidate polymorphisms in the amount of time it would take to analyze a single polymorphism individually. As for single nucleotide polymorphisms analysis, currently, high throughput assessment of SNPs in a complex sample such as the human genome often requires a complexity reduction step (i.e., a representation or subset of the genome is analyzed) and/or requires amplification via methods like PCR. Researchers could benefit from the development of a high throughput means for analyzing SNPs in human genomic DNA, without a requirement for complexity reduction or amplification.

This disclosure relates in part to a method of SNP analysis using a site-specific nicking endonuclease and to the design of specific embodiments of said method.

SUMMARY

A method of genome analysis is provided. In certain embodiments, the method comprises: a) contacting a sample comprising double-stranded genomic DNA with a site-specific nicking endonuclease that recognizes a nucleotide sequence that comprises a single nucleotide polymorphism (SNP) in the double stranded genomic DNA to provide a contacted genomic sample, in which the endonuclease nicks the genomic DNA at a nick site that is proximal to the SNP only if a first allele of the SNP is present; b) denaturing the contacted genomic sample to provide a denatured genomic sample; c) contacting under hybridization conditions the denatured genomic sample with an array of probes comprising a first probe and a second probe, in which: i) the first probe hybridizes to a nucleotide sequence comprising the SNP in a first strand of the genomic DNA; and ii) the second probe hybridizes to a nucleotide sequence in a second strand of the genomic DNA in which the second strand is complementary to the first strand; and iii) nicking at the nick site by the site-specific nicking endonuclease results in less binding of the denatured genomic sample to the first probe relative to a denatured genomic sample that is not nicked at the nick site; and d) comparing the amount of hybridization to the first probe to the amount of hybridization to the second probe, in which decreased binding of the denatured genomic samples to the first probe relative to the second probe indicates that the first allele of the SNP is present.

BRIEF DESCRIPTION OF THE FIGURES

FIG. 2 schematically illustrates an embodiment of the method described herein. FIG. 2A from top to bottom SEQ ID NOS: 1-2. FIG. 2B from top to bottom SED ID NOS: 1-2. FIG. 2C from top to bottom SEQ ID NOS: 3-4.

DEFINITIONS

Figure 1:
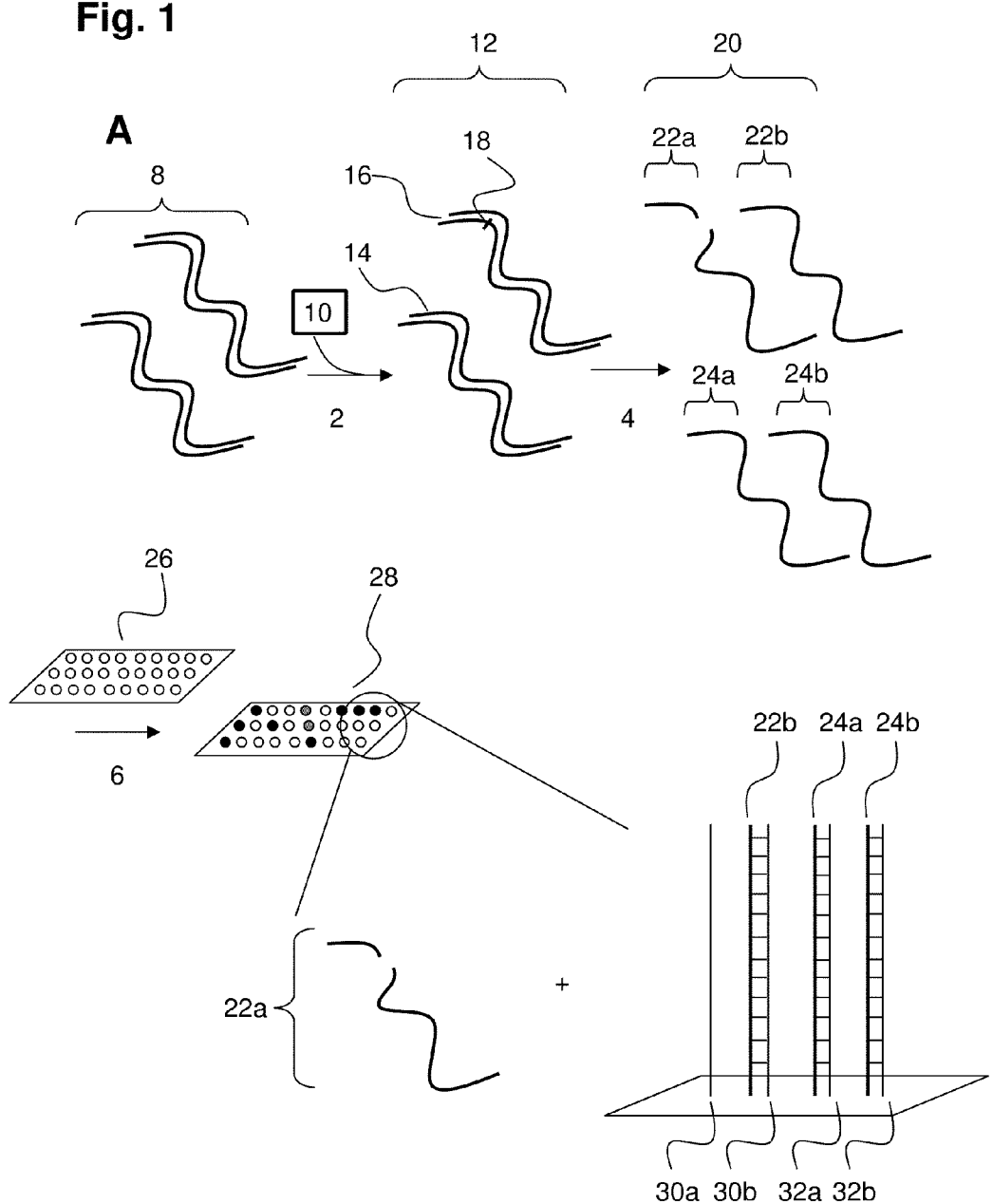
FIG. 1 schematically illustrates certain features of some embodiments of the method described herein.

The term "sample", as used herein, relates to a material or mixture of materials, typically, although not necessarily, in liquid form, containing one or more analytes of interest.

The term "genome", as used herein, relates to a material or mixture of materials, containing genetic material from an organism. The term "genomic DNA" as used herein refers to deoxyribonucleic acids that are obtained from an organism. The terms "genome" and "genomic DNA" encompass genetic material that may have undergone amplification, purification, or fragmentation. The "genome" in the sample that is of interest in a study may encompass the entirety of the genetic material from an organism, or it may encompass only a selected fraction thereof: for example, a genome may encompass one chromosome from an organism with a plurality of chromosomes.

The term "genomic region" or "genomic segment", as used herein, denotes a contiguous length of nucleotides in a genome of an organism.

The term "reference," as used herein refers to a genome, a genomic region, or a nucleotide acid to which a sample may be compared. In certain cases, the reference contains a region of known nucleotide sequence, e.g. a chromosomal region whose sequence is deposited at NCBI's Genbank database or other databases, for example. The reference may be the same species as that of the sample analyzed in the subject method.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are under 10 to 50 nucleotides in length. Oligonucleotides may contain ribonucleotide monomers (i.e., may be oligoribonucleotides) or deoxyribonucleotide monomers. Oligonucleotides may be 10 to 20, 11 to 30, 31 to 40, 41 to 50, 51-60, 61 to 70, 71 to 80, 80 to 100, 100 to 150 or 150 to 200, up to 500 or more nucleotides in length, for example.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to a target. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

An "array," includes any two-dimensional or substantially two-dimensional (as well as a three-dimensional) arrangement of addressable regions, e.g., spatially addressable regions or optically addressable regions, bearing nucleic acids, particularly oligonucleotides or synthetic mimetics thereof, and the like. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 μm$^2$, or even smaller. For example, features may have widths (that is, diameter, for a round spot) in the range from a 10 ìm to 1.0 cm. In other embodiments each feature may have a width in the range of 1.0 ìm to 1.0 mm, usually 5.0 ìm to 500 ìm, and more usually 10 ìm to 200 ìm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulsejets of either precursor units (such as nucleotide or amino acid monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. Patent Application Publication No. 20040203138 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, that could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+]+0.41$ (fraction G+C)$-(60/N)$, where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes may also be used depending on various hybridization conditions.

As used herein, the term "$T_m$-matched" refers to a plurality of nucleic acid duplexes having $T_m$s that are within a defined range, e.g. ±5° C., ±10° C., or ±15° C.

The term "hybridization conditions" as used herein refers to hybridization conditions that are optimized to anneal an oligonucleotide of a sufficient length to a probe, e.g. an oligonucleotide that is not nicked and has a contiguous length of at least 20 nucleotides (e.g. at least 30, at least 40, up to at least 50 or more) complementary to a nucleotide sequence of the probe. The hybridization conditions provide for dissociation of duplexes that anneal over a short length of region (e.g. less than 50, less than 40, less than 30, or less than 20 contiguous nucleotides) but not dissociation of duplexes formed between an un-nicked strand and its respective probe. Such conditions may differ from one experiment to the next depending on the length and the nucleotide content of the complementary region. In certain cases, the temperature for low-stringency hybridization is 5°-10° C. lower than the calculated $T_m$ of the resulting duplex under the conditions used. Details on the hybridization conditions suitable in accordance with the embodiments in the present disclosure may be found in US Patent Publication 20090035762, disclosure of which is incorporated herein by reference.

As used herein, the term "endonuclease" refers to a family of enzymes that has an activity described as EC 3.1.21, EC 3.1.22, or EC 3.1.25, according to the IUBMB enzyme nomenclature. Site-specific endonucleases recognize specific nucleotide sequences in double-stranded DNA. Some sequence-specific endonucleases cleave only one of the strands in a duplex and are referred to herein as "nicking endonucleases". Nicking endonuclease catalyzes the hydrolysis of a phosphodiester bond, resulting in either a 5' or 3' phosphomonoester.

A "site-specific nicking endonuclease", as used herein, denotes a nicking endonuclease that cleaves (e.g. nicks) one strand of a double-stranded nucleic acid by recognizing a specific sequence on the nucleic acid. The cleavage site (e.g. "nick site") of the phosphodiester backbone may fall within or proximal (e.g. no more than 1, no more than 2, no more than 4, or no more than 5 nucleotides away) to the nucleotide sequence recognized by the site-specific nicking endonuclease. In certain cases, the nucleotide sequence recognized by a site-specific nicking endonuclease comprises a specific allele of an SNP and the presence of the specific SNP allele determines whether the double-stranded DNA would be nicked.

The term "recognition site" of a site-specific nicking endonuclease, as used herein, refers to a genomic locus that is predicted or known to have a nucleotide sequence recognized by a site-specific nicking endonuclease. The "recognition site" of the site-specific nicking endonuclease employed in the subject method also contains an SNP.

As used herein, the term "single nucleotide polymorphism", or "SNP" or "SNP site" for short, refers to the single nucleotide position in a genomic sequence for which two or more alternative alleles are present at appreciable frequency (e.g., at least 1%) in a population. An "SNP allele" refers to the identity of the nucleotide of SNP. A "first allele" and a "second allele" of a SNP are different alleles, i.e., they have different SNP nucleotides.

When a site-specific nicking endonuclease nicks near a SNP "only if a first allele is present", the site-specific nicking endonuclease nicks at a first allele of the SNP and not at a different (i.e., second) allele of the SNP.

The term "strand" as used herein refers to a nucleic acid made up of nucleotides covalently linked together by phosphodiester bonds. One strand of nucleic acid does not include base-pairing nucleotides that are associated solely through hydrogen bonding, although that strand may be base-paired with a complementary strand via hydrogen bonding.

The nucleic acid of a genome exists in a double-stranded form, and as such, has two complementary strands of nucleic acid. One of the two complementary strands may be referred herein as a "first" strand and the other as the "second" strand. In certain cases, complementary strands may be referred to as "plus" and "minus" strands, the "top" and "bottom" strands or the "sense" and "antisense" strands. The first and second strands are distinct molecules, and the assignment of a strand as being a first or second strand is arbitrary and does not imply any particular orientation, function, or structure.

The term "first strand," as used herein, refers to either strand of a nucleic acid but not both strands of a nucleic acid. The term "second strand," as used herein, refers to the strand that is complementary to the "first strand".

The term "homozygous" denotes a genetic condition in which identical alleles reside at the same loci on homologous chromosomes. In contrast, "heterozygous" denotes a genetic condition in which different alleles reside at the same loci on homologous chromosomes.

"Color", as used herein, refers to the wavelength at which the emission spectrum of a label reaches a maximum. For example, a label that is referred herein as red has an emission spectrum with a maximum at about 650 nm.

As used herein, the term "data" refers to refers to a collection of organized information, generally derived from results of experiments in lab or in silico, other data available to one of skilled in the art, or a set of premises. Data may be in the form of numbers, words, annotations, or images, as measurements or observations of a set of variables. Data can be stored in various forms of electronic media as well as obtained from auxiliary databases.

DESCRIPTION OF EXEMPLARY EMBODIMENTS

A method of genome analysis is provided. In certain embodiments, the method comprises: a) contacting a sample comprising double-stranded genomic DNA with a site-specific nicking endonuclease that recognizes a nucleotide sequence that comprises a single nucleotide polymorphism (SNP) in the double stranded genomic DNA to provide a contacted genomic sample, in which the endonuclease nicks the genomic DNA at a nick site that is proximal to the SNP only if a first allele of the SNP is present; b) denaturing the contacted genomic sample to provide a denatured genomic sample; c) contacting under hybridization conditions the denatured genomic sample with an array of probes comprising a first probe and a second probe, in which: i) the first probe hybridizes to a nucleotide sequence comprising the SNP in a first strand of the genomic DNA; and ii) the second probe hybridizes to a nucleotide sequence in a second strand of the genomic DNA in which the second strand is complementary to the first strand; and iii) nicking at the nick site by the site-specific nicking endonuclease results in less binding of the denatured genomic sample to the first probe relative to a denatured genomic sample that is not nicked at the nick site; and d) comparing the amount of hybridization to the first probe to the amount of hybridization to the second probe, in which decreased binding of the denatured genomic samples to the first probe relative to the second probe indicates that the first allele of the SNP is present.

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Genome Analysis

A method of genome analysis is provided. In certain embodiments, the method comprises: a) contacting a sample comprising double-stranded genomic DNA with a site-specific nicking endonuclease that recognizes a nucleotide sequence that comprises a single nucleotide polymorphism (SNP) in the double stranded genomic DNA to provide a contacted genomic sample, in which the endonuclease nicks the genomic DNA at a nick site that is proximal to the SNP only if a first allele of the SNP is present; b) denaturing the contacted genomic sample to provide a denatured genomic sample; c) contacting under hybridization conditions the denatured genomic sample with an array of probes comprising a first probe and a second probe, in which: i) the first probe hybridizes to a nucleotide sequence comprising the SNP in a first strand of the genomic DNA; and ii) the second probe hybridizes to a nucleotide sequence in a second strand of the genomic DNA in which the second strand is complementary to the first strand; and iii) nicking at the nick site by the site-specific nicking endonuclease results in less binding of the denatured genomic sample to the first probe relative to a denatured genomic sample that is not nicked at the nick site; and d) comparing the amount of hybridization to the first probe to the amount of hybridization to the second probe, in which decreased binding of the denatured genomic samples to the first probe relative to the second probe indicates that the first allele of the SNP is present.

One embodiment chosen to illustrate the subject method is shown in FIG. 1 and described in greater detail below. With reference to FIG. 1, the method may involve contacting 2 a sample comprising double-stranded genomic DNA 8 with site-specific nicking endonuclease 10 under conditions suitable for the site-specific nicking endonuclease to nick the backbone (i.e. hydrolyzes a phosphodiester bond in the DNA backbone) in a sequence specific manner. The recognition site of site-specific nicking endonuclease 10 contains the single-nucleotide polymorphism under study. If a nucleotide sequence containing a specific SNP in the sample is recognized by the site-specific nicking endonuclease, a nick (e.g. nick 18) is generated in one strand of the double-stranded DNA. If the double-stranded genomic DNA does not contain the nucleotide sequence recognized by the site-specific nicking endonuclease at the recognition site, no nick is generated in the double-stranded DNA (e.g. double-stranded DNA 14). Accordingly, a nicked double-stranded DNA (e.g. double-stranded DNA 16 with nick 18) is an indication that a particular SNP allele is present. The sample containing the genomic DNA contacted with the site-specific nicking endonuclease 10 is then denatured in step 4 to provide denatured sample 20. Denatured sample 20 contains single strands of genomic DNA such as strands 22a, 22b, 24a, and 24b, in which single strands 22a and 22b are derived from nicked double-stranded DNA 16 and strands 24a and 24b are derived from un-nicked double-stranded DNA 14. As seen in the figure, because of nick 18 in the double-stranded DNA 16, single strand 22a is made up of two discontiguous pieces of DNA, unlike its complementary strand 22b or strands 24a and 24b derived from un-nicked double-stranded DNA 14. After the denaturation step 4, the subject method involves contacting 6 the denatured sample to array 26 containing first probe 30a and second probe 30b. First probe 30a is complementary to strand 22a, while second probe 30b is complementary to strand 22b. Since strands 22a and 22b are complementary to each other, first probe 30a and second probe 30b are also at least partially complementary to each other. Because strand 22a is broken in two pieces, the duplex formed between strand 22a and first probe 30a has a lower $T_m$ than the $T_m$ of the duplex formed between strand 22b and second probe 30b. As a result, strand 22a may not hybridize as efficiently to first probe 30a as strand 22b to second probe 30b. On the other hand, strands 24a and 24b derived from un-nicked double-stranded DNA 14, hybridize to both first probe 32a and second probe 32b respectively, equally efficiently. This is because strands 24a and 24b are not nicked and form duplexes that have the same $T_m$s. As such, comparing the amount of hybridization signal between the first probe and second probe is informative of whether a strand is nicked and consequently, of the SNP identity.

As shown in FIG. 1, the contacting step 2 may be performed by contacting a genomic sample comprising double-stranded DNA 8 with site-specific nicking endonuclease 10. In certain cases, the double-stranded DNA in the genomic sample may have been fragmented by sonication or nebulization (e.g. to a size of about 10 kb to about 1000 kb or more), amplified, or partially purified prior to the contacting step 2. Methods of amplification may involve direct and/or indirection amplifications, such as PCR and/or cloning. Methods of isolating genomic DNA may involve purifying from a crude extract to result in a partial genome containing only one, only two, only three, only four, or more chromosomes but not every chromosome in an organism.

The double-stranded genomic DNA 8 may also be treated with a ligase prior to contacting step 2 to avoid spurious nicking of sites not specifically nicked by the site-specific nicking endonuclease 10. In certain embodiments, the double-stranded DNA in the genomic sample is labeled prior to contacting step 2 or contacting step 4. In certain cases, contacting step 2 or 4 may be performed simultaneously with a labeling reaction to label the double-stranded DNA in the sample. In certain cases, the double-stranded DNA in the genomic sample is also contacted with one or more restriction endonucleases. Methods of using restriction endonucleases that may be incorporated into the various embodiments set forth in the present disclosure are described in greater detail in a U.S. Patent Application Pub. No. 20090035762, disclosure of which is incorporated herein by reference.

The way and order of contacting the genomic sample with the site-specific nicking endonuclease may vary depending on the assay conditions. In certain cases, the site-specific nicking endonuclease may be added to a sample comprising the double-stranded DNA. In other cases, the sample comprising the double-stranded DNA may be added to a solution containing the site-specific nicking endonuclease. Conditions and reagents suitable for the nicking activity of site-specific nicking endonuclease are known to one of skilled in the art. Exemplary methods and experimental conditions suitable for an active site-specific nicking endonuclease may be found in Jo K et al. (2007) *PNAS* 104:2673-2678 and Xiao M et al. (2007) *Nucleic Acids Res.* 35:e16.

Figure 3A:
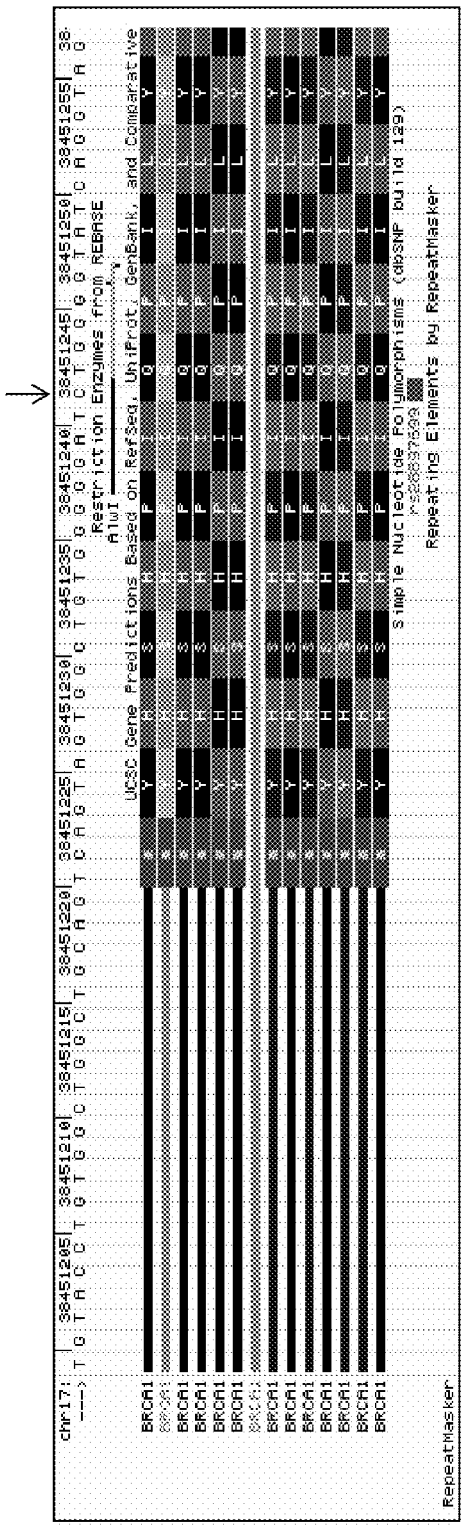
FIG. 3, panel A shows an SNP (C/A) pointed to by an arrow which is in a recognition sequence (SEQ ID NO. 5) of a site-specific nicking endonuclease Nt. AlwI in chromosome 17:38,451,200-38,451,258. Panel B shows an SNP (A/C) pointed to by an arrow which is in a recognition sequence (SEQ ID NO. 6) of a site-specific nicking endonuclease Nb.Bsm I in chromosome 17:38,499,903-38,499,951.
Figure 3B:
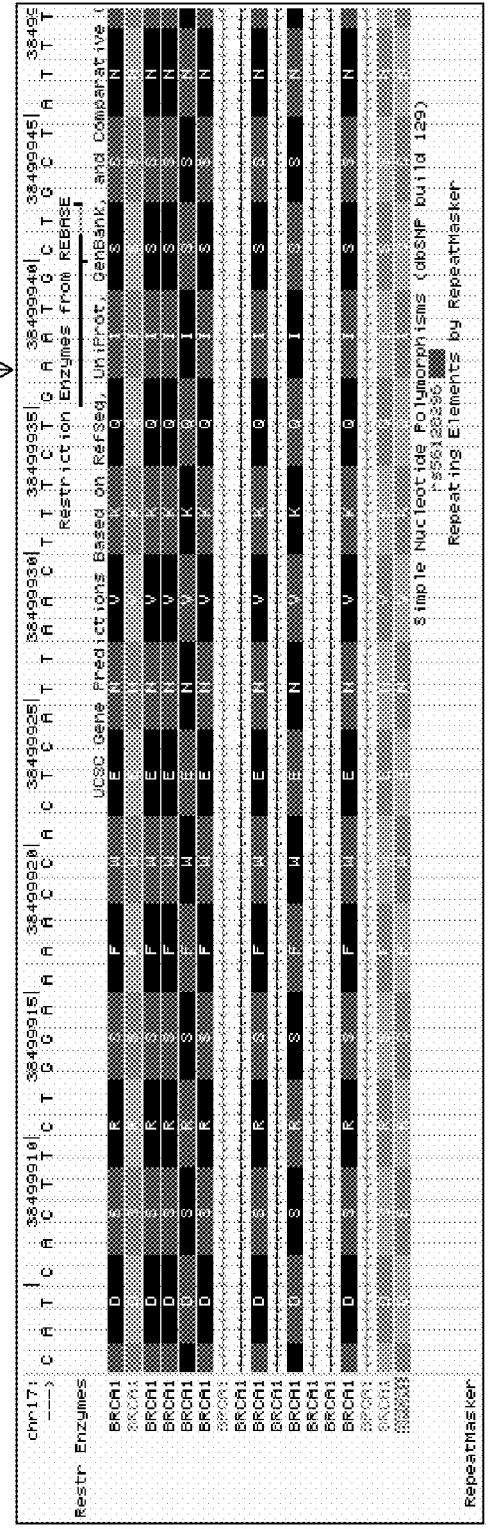

As noted above, the site-specific nicking endonuclease employed in contacting step 2 nicks the backbone of a double-stranded DNA in a sequence specific manner. The site-specific nicking endonuclease employed in the subject method recognizes a nucleotide sequence comprising a specific SNP nucleotide. In other words, the site-specific nicking endonuclease employed in the subject method recognizes a specific allele of an SNP and nicks in or proximal to the nucleotide sequence containing the SNP. Hence, the presence of a specific allele of an SNP determines whether the site-specific nicking endonuclease would nick a strand in a double-stranded DNA. Two exemplary SNPs that are located in the recognition sequences of commercially available site-specific nicking endonucleases are shown in FIG. 3.

The recognition sequence varies from one site-specific endonuclease to another so different site-specific endonuclease may be employed for interrogating different nucleotide sequences containing an SNP. Some site-specific nicking endonucleases along with their features are summarized in Table 1 below.

TABLE 1

Nicking endonucleases
(recognition sequences are presented 5'--3'.)

| Nicking endonuclease | Recognition sequence | Nick in top or bottom strand |
|---|---|---|
| Nb.BbvCI | CCTCAvGC (SEQ ID NO. 7) | Bottom |
| Nb.BsmI | GAATGvC (SEQ ID NO. 8) | Bottom |
| Nb.BsrDI | GCAATGv (SEQ ID NO. 9) | Bottom |
| Nb.BtsI | GCAGTGv (SEQ ID NO. 10) | Bottom |
| Nt.AlwI | GGATCNNNN^ (SEQ ID NO. 11) | Top |
| Nt.BbvCI | CC^TCAGC (SEQ ID NO. 12) | Top |
| Nt.BspQI | GCTCTTCN^ (SEQ ID NO. 13) | Top |
| Nt.BstNBI | GAGTCNNNN^ (SEQ ID NO. 14) | Top |

In the table above, the "v" or "^" within each recognition sequence represents the location of the nick site for the corresponding site-specific nicking endonuclease relative to the recognition sequence. "v" denotes a nick site on the strand opposite of the recognition sequence, while "^" denotes a nick site on the same strand of the recognition sequence. Details of employing site-specific nicking endonucleases may also be found in a U.S. patent application Ser. No. 12/495,199 filed on Jun. 30, 2009, disclosure of which is incorporated herein by reference.

In certain embodiments, the method may employ more than one site-specific nicking endonuclease, e.g. two, three, or more different types of site-specific nicking endonucleases, in the contacting step 2. Where more than one site-specific nicking endonuclease is used to nick a double-stranded DNA of a genomic sample, more than one type of nucleotide sequence containing an SNP may be interrogated simultaneously. Any of the site-specific nicking endonucleases including those listed in Table 1 may be employed as the additional site-specific nicking endonuclease.

After being contacted with a site-specific nicking endonuclease, the double-stranded DNAs 14 and 16 are denatured 4 into single strands. Denaturation, also referred to as DNA melting, is the process by which double-stranded DNA unwinds and separates into single strands through the disruption of hydrogen bonds between bases. Methods of denaturation are known in the art and need not be described in detail herein. Exemplary methods include the use of heat and/or detergents. See, e.g. Bowtell and Sambrook, 2002, DNA Microarrays: A Molecular Cloning Manual, Cold Spring Harbor Laboratory Press; 1st edition. One factor that may be taken into account while carrying out the denaturing step is the melting temperature ($T_m$) of the duplex that is to be melted. $T_m$ depends on both the length of the molecule and the specific nucleotide sequence composition of that molecule. As noted above, $T_m$ may be calculated using the formula $T_m=81.5+16.6(\log_{10}[Na^+])+0.41$ (fraction G+C)−(60/N), where N is the chain length and $[Na^+]$ is less than 1 M. Other ways to denature double-stranded DNA may include decreasing salt concentration, use of detergents such as urea, use of organic solvents such as dimethyl sulfoxide and formamide, or high pH, and any other methods that disrupt the hydrogen bonding between DNA strands.

As mentioned above, if the site-specific nicking endonuclease recognizes a particular SNP in a nucleotide sequence of the double-stranded DNA, a nick in one strand would be generated. Depending on the nicking endonuclease used, the nicked strand may be the same strand or the opposite strand of the recognition sequence (see Table 1) and the un-nicked strand would be complementary to the nicked strand. For ease of reference, the nicked strand may also be arbitrarily named as the first strand and the un-nicked strand the second strand. A first strand is also complementary to the second strand. However, the naming of the first or second strand is not an implication relating to the 5'→3' orientation or to the convention in designating the plus and minus strands in a double-stranded DNA. In the example shown in FIG. 1, nicked strand 22a would be referred to as the first strand while strand 22b as the second strand. In a case where no nick is generated such as in double-stranded DNA 14, either strand 24a or 24b may be referred to as the first strand and the other the second strand. For the purpose of describing various embodiments set forth below, strands 22a and 24a would be referred to as first strands and strands 22b and 24b as second strands. In certain embodiments, a nicked strand would also be referred herein as a first strand.

As seen in FIG. 1, after denaturation, the single strands are contacted 6 under hybridization conditions with an array of probes. The strands are contacted with an array under hybridization conditions optimized for the annealing between un-nicked strands and their respective probes and for the dissociation of nicked strands or oligonucleotides of a length shorter than un-nicked strands and their respective probes. Exemplary hybridization conditions are described previously and may be found in US Patent Publication 20090035762, disclosure of which is incorporated herein by reference.

Array 26 contains a first probe and a second probe. A first probe is complementary to a nucleotide sequence of a first strand while the second probe is complementary to nucleotide sequence in a second strand. The first probe may have a nucleotide sequence that hybridizes to a nucleotide sequence comprising the SNP under study in a first strand of the genomic DNA while the second probe may have a nucleotide sequence that hybridizes to a nucleotide sequence comprising the SNP in a second strand. In the embodiment shown, array 26 contains two sets of a first probe and a second probe, in which first probes 30a and 32a contain nucleotide sequences complementary to the two first strands (22a and 24a, respectively) and the second probes 30b and 32b contain nucleotide sequences complementary to the two second strands (22b and 24b, respectively). For the purpose of describing various embodiments herein, probes containing a nucleotide sequence complementary to a first strand would be referred to as first probes and probes containing a nucleotide sequence complementary to a second strand would be referred to as second probes. As mentioned above, the designation of a probe as first or second is arbitrary and does not imply a specific orientation or a plus/minus strand complementarity of the probe.

Because a site-specific nicking endonuclease nicks only one strand in a double-stranded DNA, at least one strand in any double-stranded DNA would always be un-nicked regardless of the SNP identity. The un-nicked strand (e.g. 22b or 24b), when hybridized to the respective probe, is used as a reference hybridization signal in the comparison step in the subject method. Since the strength of hybridization signal from one strand is compared with that of a complementary strand, normalization is carried out in the context of the genomic sample under study. As such, normalization in accordance with the subject method is not affected by copy number variations that exist among different genomic samples. If the un-nicked strand is not used as a reference hybridization signal as disclosed herein, the assay may often lead to erroneous SNP analysis because there is no proper reference to normalize between different genomic samples without also assessing the copy number variations. For example, if a nucleotide sequence containing an SNP exists in ten copies in genomic sample 1, while the same sequence containing the same SNP exists in one copy in genomic sample 2, genomic sample 1 may give ten times the signal as genomic sample 2. In such a case, it would be difficult to determine the presence of the SNP in sample 2 based on the relatively low signal. However, according to the present disclosure, the normalization would be based on the hybridization signal of a complementary strand of a nucleotide sequence containing the SNP. In the example above, genomic sample 1 containing ten copies of the SNP would have a reference that is ten times as strong as the reference in genomic sample 2. As such, analysis of SNP in each sample may be based on a normalization scheme unaffected by copy number variations.

As noted above, a step of the subject method following array hybridization involves comparing the amount of hybridization to the first probe to the amount of hybridization to the second probe. This comparison using the amount of hybridization the second probe as a normalizing reference would help to identify the SNP. As seen in the blown-up image of hybridized array 28, strand 22a does not hybridize to its respective probe 30a as efficiently as other strands to their respective probes due to the lower $T_m$ of a nicked strand. As such, when compared to the amount of hybridization to second probe 30b, the signal of first probe 30a is lower. This lower signal indicates that first strand is a nicked strand and thus contains the particular SNP allele recognized by the site-specific nicking endonuclease. Since the nucleotide sequence recognized by the site-specific nicking endonuclease is known, the identity of the SNP then can be determined.

However, in a scenario in which the SNP recognized by the site-specific nicking endonuclease is not present, there would not be a nicked strand, exemplified by the un-nicked double-stranded DNA 14. Both first and second strands derived from denaturing such un-nicked double-stranded DNA would hybridize equally efficiently to their respective probes, as shown by the hybridization of strand 24a to probe 32a and strand 24b to probe 32b. Accordingly, in a case where the hybridization signal of the first probe is the same as that of the second probe, the double-stranded DNA is not nicked and it is an indication that the SNP allele recognized by the site-specific endonuclease is absent.

Another example that depicts an embodiment of the subject method in detail is set forth in FIG. 2. In FIG. 2, panel A presents a double-stranded DNA in which a nucleotide sequence is boxed as the nucleotide sequence recognized by the site-specific nicking endonuclease Nb. Bsm I. The triangle indicates the nick site of Nb. Bsm I on the double-stranded DNA, and the underlined nucleotide is the SNP. Panel B in FIG. 2 depicts a scenario in which the double-stranded DNA has adenine as the SNP nucleotide, which is an allele specifically recognized by Nb. Bsm I. The first strand is then nicked, resulting in two discontiguous pieces. The two pieces from the nicked first strand would each have a lower $T_m$ when hybridized to a probe due to their shorter lengths compare to an otherwise un-nicked strand. As indicated in panel B, each of the two pieces has a $T_m$ of 58° C. or 59° C., while the second strand when hybridized to a second probe has a $T_m$ of 71° C. Under selective hybridization conditions, the two pieces from the first strand would not hybridize as well as the un-nicked second strand. A comparison of the two signals will reveal that the first probe has a signal that is lower than that of the second probe. This indicates that a particular SNP (adenine) that is recognized by the site-specific nicking endonuclease is present.

However, if the SNP nucleotide is cytosine as shown in panel C, and not the adenine that makes up the recognition sequence of Nb. Bsm I, Nb. Bsm I would no longer recognizes the nucleotide sequence comprising the SNP and would not nick any strand in the double-stranded DNA shown. In this case, both the first strand and second strand would have the same $T_m$ (e.g. 71° C.) and would hybridize equally efficiently to their respective probes.

The data from the comparing step may also provide a ratio that can help determine the genotype of a genomic sample. In certain embodiments, the ratio is the amount of signal from the hybridization of a first probe to that of the second probe. Several embodiments are presented below in which there are two alleles of the SNP being analyzed in the genomic sample.

With reference to FIG. 1, double-stranded DNA 14 and 16 may represent two different alleles of the same genomic locus. The allele that is presented by double-stranded DNA 16 has an SNP in a nucleotide sequence recognized by the site-specific nicking endonuclease so a nicked strand 22a is produced following the denaturation step. As for double-stranded DNA 14, the SNP is different from the SNP nucleotide present in double-stranded DNA 16 and is not recognized by the site-specific nicking endonuclease so neither strand 24a nor 24b would be nicked. The strands are then hybridized to an array. As explained previously, array 26 comprises first probes and second probes. First probes 30a and 32a contain the nucleotide sequence that hybridizes to first strands 22a and 24a. Similarly, second probes 30b and 32b contain the nucleotide sequence that hybridizes to second strands 22b and 24b. Upon hybridization, as shown in the blown-up image, first strand 22a would not hybridize as efficiently as second strands. As a result, there is 50% less binding of first strands (e.g. strand 22a and 24a) to first probes (e.g. 30a and 32a) compare to the binding of second strands (22b and 24b) to second probes (30b and 32b). In this embodiment, the ratio of hybridization signals of first probes to second probes would be 1:2. A ratio of 1:2 in a diploid organism would indicate that the genotype is heterozygous at the locus of the SNP recognized by the site-specific nicking endonuclease.

In an embodiment where SNP sites for both alleles do not contain the SNP nucleotide recognized by the site-specific nicking endonuclease, there would be no nicked strands so all first strands and second strands would hybridize equally efficiently to their respective probes. The ratio of the amount of hybridization to the first probe to the amount of hybridization to the second probe would then be 1:1. Where the SNP has two different alleles, a ratio of 1:1 in a diploid organism suggests that the genotype is homozygous at the locus of the SNP.

Similarly, if both alleles in the genomic sample contain the SNP nucleotide at the recognition sites of the site-specific nicking endonuclease, all first strands would be nicked. In an embodiment where all first strands are nicked, the hybridization signal of first probes as compared to that of second probes would be close to zero. A zero or near zero hybridization signal from first probes relative to the hybridization signal from second probes indicates that that the genotype is homozygous for the SNP and the SNP nucleotide is the allele that is recognized by the site-specific nicking endonuclease.

In certain embodiments, the subject method further includes measuring copy numbers of specific nucleotide sequences in combination with determining the SNP based on the embodiments described above. In certain cases, the copy number variation may be analyzed using a different array from the array of probes containing the first probe and the second probe described above. In other cases, the analysis of copy number variants may also be carried out using the same array, where the hybridization signals of the first probes and/or second probes are also used to calculate copy numbers in the genomic sample. Additional features may be optionally included on the array to facilitate the analysis. Methods and composition used for assessing copy numbers are described in detail in U.S. Patent Application Pub. Nos. 20070238106 and 20070238108, disclosures of which are incorporated herein by reference.

As noted previously, the subject method involves the analysis of a double-stranded DNA in a genomic sample. The genomic DNA may undergo staining, shearing, fragmentations, purification, etc., prior to being contacted with the site-specific nicking endonuclease in the method. In certain embodiments, the double-stranded DNA contacted with the site-specific nicking endonuclease has a contiguous stretch of at least 15, at least 20, at least 50, at least 100, at least 500, up to 1000 or more nucleotides in length. Un-nicked single strands that are contacted with an array in the subject method is at least 15, at least 20, at least 50, at least 100, at least 500, up to at least 1000 or more nucleotides in length.

The site-specific nicking endonuclease that may be used in the subject method includes any nuclease the specifically nicks the backbone of one strand of a duplex DNA in a sequence specific manner. In certain embodiments, the site-specific nicking endonuclease encompasses those presented in Table 1 and derivations thereof. The site-specific nicking endonuclease employed may be a variant that exists in nature or a recombinant variant. It would be apparent to one of ordinary skill in the art the variants of site-specific nicking endonuclease that can be employed in the subject method based on numerous studies on endonucleases in the art, as illustrated in Jeltsch et al. *Trends Biotechnol.* 14:235-8, 1996. Many site-specific nicking endonucleases are known in the art and commercially available.

The site-specific nicking endonuclease may be of a bacterial restriction modification system, of a mammalian origin or a hybrid of various origins. Recognition sequences and protein sequences of exemplary bacterial or mammalian site-specific nicking endonuclease are known and deposited in databases such as the REBASE restriction enzyme database, or NCBI's GenBank database.

As noted above, in certain embodiments, the site-specific nicking endonuclease creates a nick on a strand of a double-stranded DNA in a sequence-specific manner. In certain cases, the recognition sequence may comprise 4, 5, 6, 8, up to 10 or more nucleotides or nucleotide pairs. For example as shown in Table 1, the recognition sequence of Nb.BbvCI comprises 7 nucleotides, all of which are determined while the recognition sequence of Nt.BstNBI comprises 9 nucleotides, four of which are undetermined and so can vary among different nucleic acid samples.

The method may involve labeling the double-stranded DNA or the single stranded DNA in a genomic sample. Labeling would incorporate detectable labels into the nucleic acid so hybridization to an array of probes may be measured. Detectable labels are known in the art and need not described in detail herein. Briefly, exemplary detectable components include radioactive isotopes, fluorophores, fluorescence quenchers, affinity tags, e.g. biotin, crosslinking agents, chromophores, colloidal gold particles, beads, quantum dots, etc. In certain embodiments, the detectable label, such as biotin, may require incubation with a recognition element, such as streptavidin, or with secondary antibodies to yield detectable signals. In other embodiments, the detectable label, such as a fluorophore, may be detected directly without performing additional steps.

Additional fluorescent dyes of interest include: xanthene dyes, e.g. fluorescein and rhodamine dyes, such as fluorescein isothiocyanate (FITC), 6-carboxyfluorescein (commonly known by the abbreviations FAM and F), 6-carboxy-2',4',7', 4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc. (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (*Ann Clin Biochem.* 39:114-29, 2002).

In certain cases, the double-stranded DNA under study may be stained with a nonspecific label, such as an intercalating fluorescent dye or other dyes that would label DNA in a non-sequence specific manner (e.g. DAPI, Hoechst, YOYO-1, YO-PRO-1, or PicoGreen).

As discussed above, the present disclosure also provides an array to carry out the subject method. The array contains a first probe and a second probe, in which the first probe is complementary to a nucleotide sequence in a first strand of a double-stranded genomic DNA, in which the nucleotide sequence comprises a recognition site of a site-specific nicking endonuclease; b) the second probe is complementary to a nucleotide sequence in a second strand of said double-stranded genomic DNA, in which the second strand is complementary to the first strand; and c) the recognition sequence comprises an SNP; and e) nicking of the first strand of the double-stranded genomic DNA by the site-specific nicking endonuclease results in less binding of the first strand to the first probe relative to an un-nicked strand.

Since the first strand and the second strand are complementary (e.g. at least partially complementary), the nucleotide sequences of the first probe and the second probe are at least partially complementary to each other (e.g. at least 40%, at least 50%, at least 60%, at least 70%, at least 80%, up to 100%, (completely complementary)). Each probe may be about 10 to 20, 11 to 30, 31 to 40, 41 to 50, 51-60, 61 to 70, 71 to 80, 80 to 100, 100 to 150 or 150 to 200, up to 500 or more nucleotides in length, for example.

A probe that is complementary to a nucleotide sequence in a strand may also hybridize to the strand. The probe is designed such that it hybridizes more efficiently to a strand not nicked by the site-specific nicking endonuclease relative to strand that is shorter in length than the un-nicked strand. The nucleotide sequence in the probe that is complementary to that of the strand may be of a contiguous length of at least 25 (e.g. at least 30, at least 40, at least 50, up to at least 60) nucleotides. A probe that hybridizes to a nucleotide sequence in a strand may be at least 80% complementary to the nucleotide sequence (e.g. at least 90%, at least 95%, up to 100% complementary). The probe may comprise a nucleotide sequence that has only 1, only 2, at most 3 nucleotide differences relative to a contiguous nucleotide sequence in the strand to be hybridized to the probe. In certain embodiments, the nucleotide in the probe that base pairs with the SNP under study may be the same as one allele of SNP, and as such, the nucleotide would be different from other alleles. For example, the nucleotide in a probe that base pairs with an SNP under study may be the same or different from the allele of the SNP recognized by the site-specific nicking endonuclease employed.

In certain cases, the nucleotide complementary to the SNP is located in the middle of the nucleotide sequence of the probe. In alternative embodiments, the nick site of the site-specific nicking endonuclease employed in the subject method is in the middle or near the middle of the nucleotide sequence of the probe. A probe may comprise about 10, about 20, about 30, up to about 40 or more nucleotides 3' to the nick site and/or 5' to the predicted nick site. In other words, there may be about 10, about 20, about 30, up to about 40 or more nucleotides on each side flanking the predicted nick site.

In certain embodiments, the probes are designed such that duplexes formed by hybridization to the first probe and to the second probe are $T_m$-matched. In many embodiments, the array contains duplicates of first probes and second probes. In related embodiments, there is a plurality of sets of first probes and second probes such that each of the plurality is directed to interrogate a different SNP. For example, there may be a first set of first probe and second probe that are complementary to a sequence comprising an SNP at a first locus in the genome while there is a second set that are complementary to a different nucleotide sequence comprising another SNP at a second locus in the genome. In certain cases, there is a number of sets to accommodate all the SNP sites that may be nicked by the site-specific nicking endonuclease employed.

In certain embodiments, the array contains additional probes other than first and second probes. As mentioned previously, different probes may be required to further carry out other types of analysis. The array may also encompass control probes that are specific for nucleotide sequences of first and second strand that do not contain nucleotide sequences containing the SNP interrogated by the site-specific nicking endonucleases.

Reading of the array may be accomplished by illuminating the array and reading the location and intensity of resulting fluorescence at each feature of the array to detect any binding complexes on the surface of the array. For example, a scanner may be used for this purpose that is similar to the AGILENT MICROARRAY SCANNER available from Agilent Technologies, Palo Alto, Calif. Other suitable apparatus and methods are described in U.S. Pat. No. 7,205,553 "Reading Multi-Featured Arrays" by Dorsel et al.; and U.S. Pat. No. 7,531,303 "Interrogating Multi-Featured Arrays" by Dorsel et al., both disclosures of which are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample or an organism from which a sample was obtained exhibits a particular condition). The results of the reading (processed or not) may be forwarded (such as by communication) to a remote location if desired, and received there for further use (such as further processing).

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart.

"Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As noted above, the subject method involves comparing the data derived from a genomic DNA sample to a reference. The reference may also undergo the subject method in the same way as the genomic sample under interest. In other cases, the reference sample is contacted to an array to provide hybridization signals as controls. Controls may indicate one or more of the following: activity of the site-specific nicking endonuclease, the hybridization efficiency of the probes, denaturing conditions; etc. The reference sequence may be synthesized or isolated from a biological source. A reference sequence may be a sequence derived from an identified source or from the same species as the genomic sample under study. The source of the reference may be known to be homozygous or heterozygous for a particular genomic locus of interest. In certain cases, the source may be wild-type for a genomic locus of interest. The source may contain an allelic variant of interest. In certain cases, the reference sequence may be known so that the alleles of the single nucleotide polymorphisms are known.

The present disclosure also provides a system for sample analysis comprising: a) reagents to perform the subject method comprising a site-specific nicking endonuclease that recognizes a nucleotide sequence comprising a SNP; b) reagents for denaturing double-stranded nucleic acids; c) hybridization chamber; d) an array of probes comprising a first probe and a second probe, in which i) the first probe is at least partially complementary to the second probe; ii) the first probe is complementary a nucleotide sequence comprising an SNP in a first strand; iii) the second probe is complementary to a second strand that is complementary to the first strand; e) an array scanner to excite and collect signals from the hybridized array.

The system may also include a computer for recording data and a computer-readable medium for storing data. The system may comprise one or more site-specific endonucleases as certain embodiments described above. The hybridization chamber and array scanner encompass any instrument employed for the array hybridization and means to collect hybridization signal known in the art.

The system may include a computer programmed to control an array scanner to excite various locations on an array and to record and store hybridization signals from an array. The system may encompass a storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer on a local or remote network. Similarly, a database of reference pattern may also be provided in a computer readable medium in the subject system.

Kits

Also provided by the present disclosure are kits for practicing the subject method as described above. The subject kit contains a site-specific nicking endonuclease that recognizes a nucleotide sequence comprising an SNP and an array comprising a first probe and a second probe as described previously. The kit may further contain a reference genome or information relating to a reference genome. The SNP identity of the reference genome may be known and provided in the information.

In additional embodiments, the kit may further comprise additional types of site specific nicking endonucleases, in which each would recognize a different SNP. In an alternative embodiment, the kit further comprises reagents for labeling double-stranded DNA or single-stranded DNA. Labels may also be provided in various color labels.

The kits may be identified by the type of site-specific nicking endonuclease, the nucleotide sequence recognized by the site specific nicking endonuclease, the SNP recognized by the site-specific nicking endonuclease, and the reference genome. The kits may also be identified by the type of organism or disease or biological conditions for which the kit is designed.

In addition to above-mentioned components, the subject kit typically further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the instructions, the kits may also include one or more control analyte mixtures, e.g., two or more control analytes for use in testing the kit.

In addition to above-mentioned components, the subject kit may include software to perform comparison of a collected hybridization signal with another.

Utility

The subject method finds use in a variety of applications, where such applications are generally nucleic acid detection applications in which the presence of a particular nucleotide sequence in a given sample is detected at least qualitatively, if not quantitatively. In general, the above-described method may be used in order to determine the nucleotide identity of the single-nucleotide polymorphism in a genomic DNA.

Since nicking is sequence dependent, the presence or absence of nicking in specific locations on double-stranded DNA and their levels of hybridization to their respective probes are informative of the SNP identity. By comparing the level of hybridization of one strand to that of a complementary strand as reference, the identity of the SNP may be determined. In some cases, the genotype of the SNP locus may also be determined based on the ratio of hybridization signals from the first probes and that from the second probes, as described previously. Using the second probe as the reference allows the signal levels to be normalized in the context of the genomic sample under study and is not affected by copy number variations that are commonly present between different genomic samples.

Analysis carried out using the method may be applied on a genomic scale that involves shearing, fragmenting, amplifying, or processing the double-stranded genomic DNA in other ways prior to contacting the genomic sample with a site-specific nicking endonuclease.

Other assays of interest which may be practiced using the subject method include: genotyping, scanning of known and unknown mutations, gene discovery assays, genomic structural mapping, differential gene expression analysis assays, nucleic acid sequencing assays, disease diagnosis and prognosis, and the like.

The data of SNP alleles identified through the use of the subject methods can also be collected and compared to a set of known SNPs associated with a disease or biological condition with the purpose of identifying an unknown source, genotyping, predicting a biological condition. This might represent comparison between SNPs coming from variants of a region to a reference. Identification of one or more SNPs in a sample genome may be useful for a wide variety of investigations, such as identifying origin of a crop, identifying species of fish or other animals, identifying pathogens, diagnosing human diseases, investigating cancer lineages or distinguishing between a finite number of known genotypes, etc.

In certain cases, the genomic sample under study may be derived from a sample tissue suspected of a disease or infection. Performing the subject method to analyze the genomic sample from such sample tissues would be useful for disease diagnosis and prognosis. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Since the nucleotide sequences of hundreds of thousands of SNPs from humans, other mammals (e.g., mice), and a variety of different plants (e.g., corn, rice and soybean), are known (see, e.g., Riva et al 2004, *A SNP-centric database for the investigation of the human genome* BMC Bioinformatics 5:33; McCarthy et al 2000 *The use of single-nucleotide polymorphism maps in pharmacogenomics* Nat Biotechnology 18:505-8) and are available in public databases (e.g., NCBI's onlsite-specific nicking endonuclease dbSNP database, and the online database of the International HapMap Project; see also Teufel et al 2006 *Current bioinformatics tools in genomic biomedical research* Int. J. Mol. Med. 17:967-73), choosing a site specific nicking endonuclease that would recognize an SNP would be well within the skill of one of skilled in the art.

The above described applications are merely representations of the numerous different applications for which the subject array and method of use are suited. In certain embodiments, the subject method includes a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method comprising:
   a) contacting a sample comprising double-stranded genomic DNA with a site-specific nicking endonuclease that recognizes a nucleotide sequence that comprises a single nucleotide polymorphism (SNP) in said double stranded genomic DNA to provide a contacted genomic sample, wherein said endonuclease nicks said genomic DNA at a nick site that is proximal to said SNP only if a first allele of said SNP is present;
   b) denaturing said contacted genomic sample to provide a denatured genomic sample;
   c) contacting under hybridization conditions said denatured genomic sample with an array of probes comprising a first probe and a second probe, wherein:
      i) said first probe hybridizes to a nucleotide sequence in a first strand of said genomic DNA, wherein said nucleotide sequence comprises said SNP; and
      ii) said second probe hybridizes to a nucleotide sequence in a second strand of said genomic DNA, wherein said nucleotide sequence comprises said SNP; and
      iii) nicking at said nick site by said site-specific nicking endonuclease results in less binding of said denatured genomic sample to said first probe relative to a denatured genomic sample that is not nicked at said nick site; and
   d) comparing the amount of hybridization to said first probe to the amount of hybridization to said second probe, wherein decreased binding of said denatured genomic samples to said first probe relative to said second probe indicates that said first allele of said SNP is present.

2. The method of claim 1, wherein said comparing step d) provides a ratio of the amount of hybridization to said first probe to the amount of hybridization to said second probe.

3. The method of claim 2, wherein said ratio of about 1:2 indicates a genotype that is heterozygous for said SNP.

4. The method of claim 2, wherein said ratio of about 1:1 or 0:1 indicates a genotype that is homozygous for said SNP.

5. The method of claim 1, further comprising measuring a copy number of a sequence comprising said SNP based on the amount of hybridization to said first probe or to said second probe.

6. The method of claim 1, wherein said first probe and said second probe have $T_m$s that are within 10° C. of one another.

7. The method of claim 1, wherein said double-stranded genomic DNA is contacted with at least two site-specific nicking endonucleases, wherein said at least two site-specific nicking endonucleases recognize different nucleotide sequences comprising an SNP.

8. The method of claim 1, wherein said array comprises multiple probe sets, wherein each set of said multiple probe sets comprises a first probe and a second probe and is for detecting a different SNP.

9. The method of claim 1, further comprising contacting a reference sample to said array of probes, wherein said nucleotide sequence comprising said SNP in said reference sample is known.

10. The method of claim 1, wherein said contacting step a) further comprises contacting said double-stranded genomic DNA with a restriction endonuclease.

11. The method of claim 1, wherein said double-stranded genomic DNA is from a human.

12. The method of claim 11, wherein said first probe or said second probe is complementary to an SNP allele that is associated with a known disease or condition.

13. The method of claim 1, wherein said double-stranded genomic DNA is isolated from a genomic sample.

14. The method of claim 1, wherein said double-stranded genomic DNA is amplified from a genomic sample.

15. The method of claim 1, further comprising fragmenting said genomic DNA prior to contacting said sample with said site-specific nicking endonuclease.

16. The method of claim 1, wherein said first and second probes hybridize with a contiguous sequence of at least 20 nucleotides in length comprising said SNP and wherein nick site of said site-specific nicking endonuclease is located at or near the middle of said contiguous sequence.

17. An array comprising a first probe and a second probe, wherein
   a) said first probe is complementary to a nucleotide sequence in a first strand of a double-stranded genomic DNA, wherein said nucleotide sequence comprises a recognition site of a site-specific nicking endonuclease;

b) said second probe is complementary to a nucleotide sequence in a second strand of said double-stranded genomic DNA, wherein said second strand is complementary to said first strand;
c) said recognition site comprises an SNP; and
e) nicking of said first strand of said double-stranded genomic DNA by said site-specific nicking endonuclease results in less binding of said first strand to said first probe relative to an un-nicked strand.

18. The array of claim 17, wherein said first probe and said second probe have $T_m$s that are within 10° C. of one another.

19. A kit for sample analysis comprising:
a) a site-specific nicking endonuclease that recognizes a nucleotide sequence comprising a SNP; and
b) an array of claim 17.

20. The kit of claim 19, further comprising a reference genomic DNA, wherein said SNP in said reference genomic DNA is known.

* * * * *

SEQUENCE LISTING

<160> NUMBER OF SEQ ID NOS: 14

<210> SEQ ID NO 1
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 1
ctggaaaacc actcattaac tttctgaatg ctgctattta gtgttatcca aggaacatct     60

<210> SEQ ID NO 2
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 2
agatgttcct tggataacac taaatagcag cattcagaaa gttaatgagt ggttttccag     60

<210> SEQ ID NO 3
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 3
ctggaaaacc actcattaac tttctgcatg ctgctattta gtgttatcca aggaacatct     60

<210> SEQ ID NO 4
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 4
agatgttcct tggataacac taaatagcag catgcagaaa gttaatgagt ggttttccag     60

<210> SEQ ID NO 5
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 5
tgtacctgtg gctggctgca gtcagtagtg gctgtggggg atctggggta tcaggtag       58

<210> SEQ ID NO 6
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 6
catcacttct ggaaaaccac tcattaactt tctgaatgct gctattt                   47

<210> SEQ ID NO 7
<211> LENGTH: 7
<212> TYPE: DNA

```
<213> ORGANISM: Artificial Sequence
<220> FEATURE:
<223> OTHER INFORMATION: Synthetic Oligonucleotide

<400> SEQUENCE: 7 cctcagc                                                                        7

<210> SEQ ID NO 8
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 8 gaatgc                                                                         6

<210> SEQ ID NO 9
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 9 gcaatg                                                                         6

<210> SEQ ID NO 10
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 10 gcagtg                                                                         6

<210> SEQ ID NO 11
<211> LENGTH: 9
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 6, 7, 8, 9
<223> OTHER INFORMATION: n = A,T,C or G

<400> SEQUENCE: 11 ggatcnnnn                                                                      9

<210> SEQ ID NO 12
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 12 cctcagc                                                                        7

<210> SEQ ID NO 13
<211> LENGTH: 8
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 8
<223> OTHER INFORMATION: n = A,T,C or G

<400> SEQUENCE: 13 gctcttcn                                                              8

<210> SEQ ID NO 14
<211> LENGTH: 9
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 6, 7, 8, 9
<223> OTHER INFORMATION: n = A,T,C or G

<400> SEQUENCE: 14 gagtcnnnn                                                             9
```